United States Patent [19]

von der Haar

[11] 4,110,320

[45] Aug. 29, 1978

[54] METHOD OF FRACTIONATING AND SEPARATING PROTEINS

[75] Inventor: Friedrich von der Haar, Bovenden, Germany

[73] Assignee: Max-Planck-Gesellschaft zur Forderung der Wissenschaften E.V., Gottingen, Germany

[21] Appl. No.: 796,050

[22] Filed: May 11, 1977

[30] Foreign Application Priority Data

May 24, 1976 [DE] Fed. Rep. of Germany ....... 2623276

[51] Int. Cl.² ............................................... A23J 1/00
[52] U.S. Cl. ............................................... 260/112 R
[58] Field of Search ................................... 260/112 R

[56] References Cited

PUBLICATIONS

Raibaud et al., FEBS Letters, 50, 130–134 (1974).
Shaltiel et al., Proc. Nat. Acad. Sci., U.S.A., 72, 3397–3401 (1975).

*Primary Examiner*—Walter C. Danison
*Attorney, Agent, or Firm*—Burgess, Dinklage & Sprung

[57] ABSTRACT

Improvement in a method for the fractionation and separation of proteins by adsorption on an organic gel and elution with a descending ammonium sulfate gradient, the improvement comprising treating a solution of the proteins with ammonium sulfate down to a concentration which is from 5 to 15% below the concentration normally required for protein precipitation, mixing the solution obtained with unsubstituted agarose gel, whereby the protein is precipitated onto the agarose gel, and then fractionally eluting the latter, preferably with a linearly descending gradient.

4 Claims, 2 Drawing Figures

METHOD OF FRACTIONATING AND SEPARATING PROTEINS

The present invention relates to a process for fractionating and separating proteins, particularly biologically active proteins.

The fractionation and separation of proteins is difficult, since they differ only gradually in the physical-chemical properties which can be utilized for their separation. In practice, therefore, a relatively limited number of methods are used in combination, since normally only a partial refinement is achieved in the individual separations. Since the individual proteins often behave quite differently in the various known methods of separation, an improvement in protein fractionation and separation might be expected if a larger number of basic methods of separation were available.

It is known that proteins can be drawn from salt solutions onto "amphiphilic" gels, amphiphilic gels being organic gels which are formed by the introduction of hydrophobic groups, such as alkyl groups, alkylamine groups, aryl groups and aralkyl groups, into hydrophilic, cross-linked gels. The hydrophilic base gels of such amphiphilic gels are, for example, cross-linked dextran, agar and agarose. It is assumed that the binding of the proteins to these hydrophobically substituted gels is based on a hydrophobic interinteraction analogous to what is known as hydrophobic chromatography, and it has been observed that the longer the carbon side chain of the hydrophobic substituent is, the stronger is this hydrophobic bond. In order to achieve a binding of the proteins, it has been found that, in general, the hydrophobic side chain must have a minimum length of three carbon atoms.

It has now surprisingly been found that, if certain very specific conditions are satisfied, such separations can be achieved with a hydrophilic gel which is not hydrophobically substituted.

The method of the invention for the fractionation and separation of proteins comprises absorption of the proteins on an organic gel and elution with a descending ammonium sulfate gradient, wherein a solution of the proteins containing ammonium sulfate in a concentration from 5 to 15% below the concentration normally required for the precipitation of the protein is mixed with unsubstituted agarose, whereby the protein is precipitated onto the agarose gel.

Agarose is a gellable polysaccharide obtained from agar, and it consists of alternating units of 1,3-linked β-D-galactopyranose and 1,4-linked 3,6-anhydro- -L-galactopyranose.

In aqueous suspension, the agarose gel is in the form of a transparent to translucent substance. If the protein solution, whose ammonium sulfate concentration is in the above-stated range and is preferably about 8 to 12% below the concentration required for protein precipitation, is combined with the agarose gel, a precipitation of the protein onto the gel surface takes place; this can be witnessed visually since it causes the gel to become opaque. The proteins precipitated onto the gel are then eluted with a descending ammonium sulfate gradient, i.e., with a diminishing ammonium sulfate concentration. Preferred here is the use of a linearly descending gradient.

The precipitation of protein on unsubstituted agarose occurring in the method of the invention is surprising, since attempts made hitherto to obtain adsorption on the principle of precipitation have failed (Proc. Nat. Acad. Sci., USA, 72, 3397 – 3401 [1975]; FEBS Letters, 50, 130 – 134 [1974]). It is assumed that this surprising finding is to be attributed to the fact that the solvatization sphere on the gel surface differs from the solvatization in solution, and therefore a protein can be precipitated ("salted out") on a surface at a lower salt concentration than is required for precipitation in solution.

The method of the invention serves preferably for the separation of biologically active proteins, such as enzymes, immunologically active proteins such as antibodies, protein hormones, and the like. Nevertheless, biologically inactive, soluble proteins can be separated or refined by this method as well. In the elution with diminishing ammonium sulfate concentration, the precipitated proteins are redissolved successively, a good separation and fractionation even of closely related proteins being achieved. A special advantage of the method of the invention consists in the very high yield of enzymatic activity, plus good reproducibility and good purification factors.

EXAMPLES

The invention will be described in the following examples on the basis of the separation and purification of aminoacyl-tRNA-synthetases which are specific for phenylalanyl, isoleucyl and valyl. In the appended drawing, FIG. 1 is a graphic representation of the fractionated resolution of a mixture of phenylalanyl-tRNA-synthetase and isoleucyl-tRNA-synthetase;

FIG. 2 represents the fractionated resolution of valyl-tRNA-synthetase.

EXAMPLE

Buffers used:

A: 0.2 M TRIS × HCl pH 9, containing 0.3 M $NH_4Cl$, 0.02 M mg $SO_4$, $10^{-3}$ M ethylenediaminetetraacetic acid (EDTA) 3% glucose.

B: 0.06 M potassium phosphate pH 7.2, containing $10^{-3}$ M dithioerythritol, $10^{-5}$ M phenylmethylsulfonylfluoride.

C: 0.03 M potassium phosphate pH 7.2, containing $10^{-3}$ M dithioerythritol, $10^{-5}$ M phenylmethylsulfonylfluoride and 10% (v/v) glycerine.

D: 0.03 M potassium phosphate pH 6.0, containing $10^{-3}$ M dithioerythritol, $10^{-5}$ M phenylmethylsulfonylfluoride and ammonium sulfate.

I. Recovery of the enzyme fractions used:

2 liters of buffer A were added to 6 kg of yeast (Saccharomyces cerevisiae) which had been frozen and stored at minus 20° C, and the mixture was allowed to thaw overnight. The suspension was then passed once through a Gaulin homogenizer. The cell fragments were removed by centrifugation at 17,000 g. Then 200 ml of a 10% (w/v) polyethyleneimine (adjusted to pH 6 with HCl) was added to the supernatant fluid, whereupon all of the fine cell fragments and more than 95% of the nucleic acids precipitated. The precipitate was removed by centrifugation at 17,000 g. 430 gm of solid ammonium sulfate was added per liter of supernatant liquid (70% saturation), the pH being maintained at 7.0. The precipitate was again centrifuged out at 17,000 g, dissolved in buffer B, and dialyzed overnight against 5 liters of buffer B. The dialyzate was diluted with one volume of water and put through a column of molecular sieve material (carboxymethylated, cross-linked dextran) with a one-liter bed volume. The column was then washed with buffer C which contained 0.05 M KCl for removal of unbound protein.

Phenylalanyl-tRNA-synthetase (E.C. 6.1.1.20) and isolecuyl-tRNA-synthetase (E.C. 6.1.1.5.) were eluted from the column with buffer C which contained 0.15 M KCl. The valyl-tRNA-synthetase (E.C. 6.1.1.9.) was eluted with buffer C containing 0.3 M KCl. The fractions obtained were brought to 70% saturation (430/1) with solid ammonium sulfate, and the precipitate was gathered.

II. Purification on agarose.

The ammonium sulfate precipitate obtained was dissolved in a minimum amount of buffer C and dialyzed against buffer D, which had been 47% saturated with ammonium sulfate. The precipitate was removed by centrifugation. The supernatant solution was placed on an agarose column of 4.5 × 17 cm which balances with buffer D 50% saturated with ammonium sulfate. Then the column was eluted with one liter of buffer D each time, with a concentration decreasing with a linear gradient from 50% ammonium sulfate to 15%. 17 milliliter fractions were collected. The results obtained are given in FIGS. 1 and 2 in the drawing and in the following table.

TABLE

Purification of the aminoacyl-tRNA-synthetases

| Enzyme | Stage | Total amount of protein ($A_{280}$ Units) | Enzyme activity (units per mg of protein*) | Enrichment factor | Total Amount of enzyme (units) |
|---|---|---|---|---|---|
| Phenyl- | Dialyzate | 50,000 | 2.20 | 1 | 110,000 |
| alanyl- | Dextran | 2,700 | 55 | 40 | 148,000 |
| tRNA-synthetase | Agarose | 380 | 342 | 155 | 130,000 |
| Isoleucyl- | Dialyzate | 50,000 | 1.20 | 1 | 60,000 |
| tRNA- | Dextran | 2,700 | 24 | 20 | 65,000 |
| synthetase | Agarose | 176 | 349 | 290 | 61,000 |
| Valyl- | Dialyzate | 50,000 | 1.40 | 1 | 70,000 |
| tRNA | Dextran | 2,000 | 40 | 28 | 80,000 |
| synthetase | Agarose | 157 | 298 | 212 | 47,000 |

*One unit is defined as the amount which aminoacylates 1 nmol of tRNA per minute.

Figure 1:
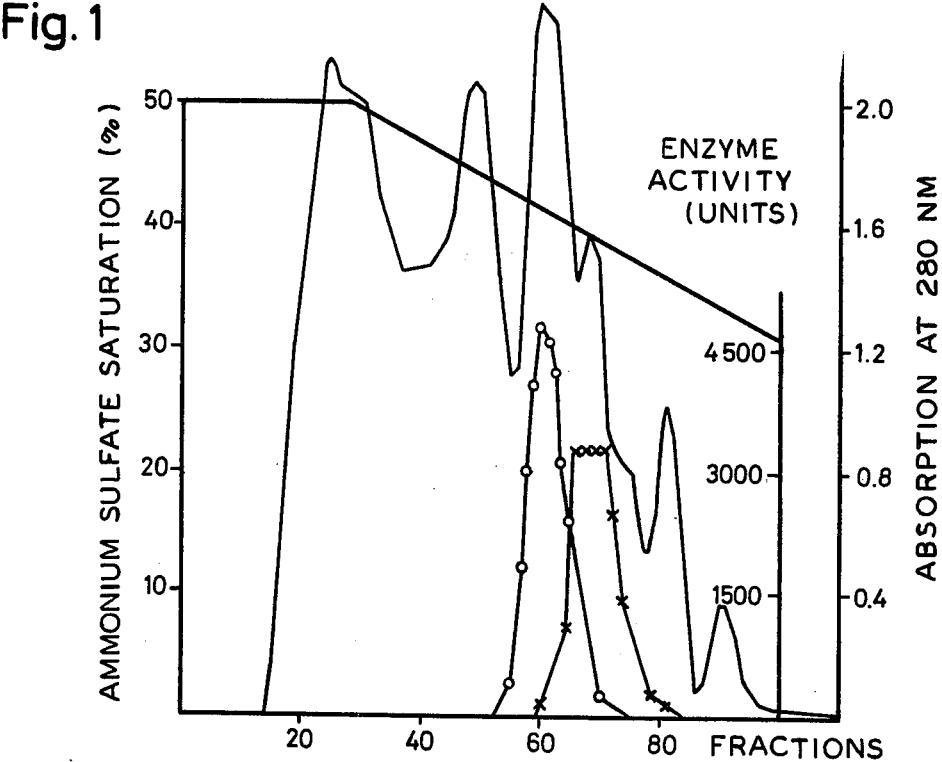
FIG. 1 shows the fractional elution of phenylalamyl-tRNA-synthetase and isolecuyl-tRNA-synthetase: — = absorption at 280 nm; o-o = activity of phenylalanyl-tRNA-synthetase; x-x = activity of isoleucyl-tRNA-synthetase.
Figure 2:
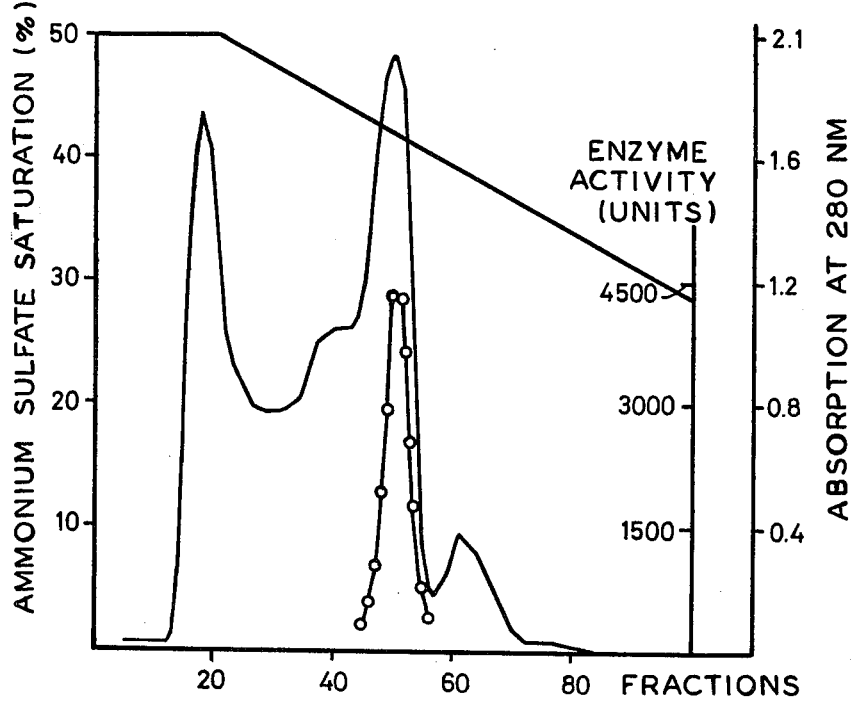
FIG. 2 shows the fractional elution of valyl-tRNA-synthetase: — = absorption at 280 nm; o-o = enzyme activity.

It will be understood that the specification and examples are illustrative but not limitative of the present invention and that other embodiments within the spirit and scope of the invention will suggest themselves to those skilled in the art.

What is claimed is:

1. In a method for the fractionation and separation of proteins by adsorption on an organic gel and elution with a descending ammonium sulfate gradient, the improvement comprising treating a solution of the proteins with ammonium sulfate down to a concentration which is from 5 to 15% below the concentration normally required for precipitation of said proteins, mixing the solution obtained with unsubstituted agarose gel, whereby the proteins are precipitated onto the agarose gel, and then fractionally eluting the latter.

2. Method as claimed in claim 1 wherein the ammonium sulfate concentration is adjusted to 8 to 12% below the concentration normally required for protein precipitation.

3. Method as claimed in claim 1 wherein the elution is performed with a linearly descending gradient.

4. Method as claimed in claim 2 wherein the elution is performed with a linearly descending gradient.

* * * * *